US006368617B1

(12) United States Patent
Hastings et al.

(10) Patent No.: US 6,368,617 B1
(45) Date of Patent: Apr. 9, 2002

(54) DIETARY SUPPLEMENT

(75) Inventors: Carl W. Hastings, Glencoe; David J. Barnes, Wildwood, both of MO (US); Christine A. Daley, Columbia, IL (US)

(73) Assignee: Reliv' International, Inc., Chesterfield, MO (US)

( * ) Notice: Subject to any disclaimer, the term of this patent is extended or adjusted under 35 U.S.C. 154(b) by 0 days.

(21) Appl. No.: 09/858,047

(22) Filed: May 15, 2001

(51) Int. Cl.$^7$ .......................... A61K 9/14; A61K 47/28; A61K 31/56
(52) U.S. Cl. ......................... 424/439; 514/168
(58) Field of Search ........................... 424/439; 514/168

(56) References Cited

U.S. PATENT DOCUMENTS

| | | | |
|---|---|---|---|
| 5,292,730 A | 3/1994 | Lardy | 514/171 |
| 5,296,481 A | 3/1994 | Partridge et al. | 514/178 |
| 5,585,371 A | 12/1996 | Lardy | 514/171 |
| 5,641,766 A | 6/1997 | Lardy | 514/171 |
| 6,048,846 A | * 4/2000 | Cochran | 514/168 |

OTHER PUBLICATIONS

Jamieson, J. et al., "The Role of Somatotroph–Specific Peptides and IGF–1 Intermediates as an Alternative to High Injections," American College for Advancement in Medicine, (Oct. 30, 1997).

* cited by examiner

*Primary Examiner*—Carlos Azpuru
(74) *Attorney, Agent, or Firm*—Marshall, Gerstein & Borun.

(57) ABSTRACT

A dietary supplement for promoting healthy hormonal balance in adult human subjects, and especially in elderly subjects, that comprises a secretagogue for stimulating the release of human Growth Hormone (hGH) by the pituitary, and the conversion by hGH to Insulin-Like Growth Factor 1(IGF-1), in combination with 7-keto dehydroepiandosterone (7-keto DHEA). The dietary supplement also includes other interacting ingredients for delivering antioxidants for retarding damage at the cellular level caused by the presence of free radicals, and natural herbs for promoting physiological health.

24 Claims, No Drawings

DIETARY SUPPLEMENT

BACKGROUND AND SUMMARY OF THE INVENTION

Human Growth Hormone (hGH), also known as somatotropin, is an endocrine hormone produced by the pituitary. Its production peaks during adolescence and diminishes with age. Upon its release from the pituitary, hGH is converted by the liver and other tissues to its growth-promoting metabolite somatomedin C, commercially known as Insulin-like Growth Factor type 1 (IGF-1), so-called because it performs an insulin-like function of promoting glucose transfer through cell membranes in cell metabolism.

It is now understood that the physiologic effects associated with hGH occur primarily through the function of IGF-1, partly because serum IGF-1 has a half-life of about 20 hours in contrast to circulating Growth Hormone with a half-life of only about 20 minutes. Several factors are known to affect hGH release and IGF-1 response, and they include the hypothalmic hormone somatostatin, which limits hGH release, and Growth Hormone Releasing Hormone (GHRH), which stimulates such release, as well as somatotroph receptors, insulin regulation, hepatic function and the availability of IGF-1 receptors sites. Jamieson, J and Dorman, L. E., The Role Of Somatotroph-Specific Peptides And IGF-1 Intermediates As An Alternative To High Injections, American College for Advancement in Medicine, Oct. 30, 1997. Correlating these factors has led to the development of a proprietary product known as Symbiotropin, available from Jamieson Designs, St. Louis, Mo. Symbiotropin is an hGH secretagogue composed of anterior pituitary peptides, sequenced glycoamino acid complex, pharmaceutical saccharides, L-alpha glycerlphosphoryl choline, a plant-derived source of L-dopa, and botanical regulators of insulin and IGF-1 that has been shown in clinical tests both to promote and modulate IGF-1 levels within a physiologic range, revealing notable improvements in patients undergoing such hormone therapy in terms of muscle size and strength, fat reduction, energy increase, exercise endurance, improvements in skin elasticity, texture, and thickness, and healing capacity.

Another hormone linked to healthy aging, including healthy immune brain and cardiovascular functions, is dehydroepiandrosterone (DHEA), the most abundant hormone in the human body. It is produced by the adrenal cortex along with other steroids such as glucocorticoids (cortisol or hydrocortisone) and mineral corticoids (aldosterone). Concerns have been expressed about its use as a dietary supplement, however, because when it is ingested it is metabolized into various metabolites, some of which may convert into active male or female sex hormones, specifically, testosterone and estrogens.

A natual metabolite of DHEA is 7-keto dehydroepiandosterone (7-keto DHEA), also known chemically as 3-beta-acetoxyandrost-5-en-7,17-dione. 7-keto DHEA is not only a potent metabolite of DHEA but, unlike DHEA, cannot be converted to active androgens and estogens. Scientific research on 7-keto DHEA demonstrates that it has therapeutic applications in immune modulation, immune enhancement through T-cell upregulation, memory enhancement, and weight loss and management by means of its theromagenic-enhancing action. For further information on 7-keto DHEA, reference may be made to U.S. Pat. Nos. 5,290,730, 5,296,481, 5,585,371, and 5,641,766, the disclosures of which are incorporated by reference herein.

SUMMARY OF THE INVENTION

It is an object of the invention to provide new orally-ingestable dietary supplements that reduce or retard the effects of aging. More specifically, the invention is concerned with dietary supplements that replenish or stimulate the production and release of hormones that promote longevity, enhance wellness, and reduce the effects of aging at the cellular level.

Along with other ingredients, the food supplements of this invention comprise both 7-keto DHEA and a secretagogue for pituitary somatotrophs that contains anterior pituitary peptides, a sequenced glycoamino acid complex, a source of L-dopa, pharmaceutical saccharides, botanical regulators of insulin and IGF-1, and L-alpha glycerylphosphoryl choline (GPC). The supplements may also contain antioxidants and natural herbal ingredients that are believed to reduce damage at the cellular level caused by free radicals and which are believed to be active in reducing memory loss, promoting healthy brain function, and eliminating harmful toxins.

DETAILED DESCRIPTION OF THE PREFERRED EMBODIMENTS

The secretagogue known as Symbiotropin (from Jamieson Designs, St. Louis, Mo.) has been found to promote hGH production by the pituitary and the release of IGF-1 in physiologic ranges, and generally to reverse many of the symptoms of human biological aging, by restoring muscle mass, decreasing body fat, thickening the skin and reducing wrinkles, increasing energy and sexual function, restoring the size of liver, pancreas, heart and other organs that shrink with age, improving vision and memory, elevating mood and improving sleep, normalizing blood pressure, increasing cardiac output and stamina, improving immune function, and assisting in wound healing. The secretagogue is known to comprise a combination of anterior pituitary peptides, a glycoamino acid complex, pharmaceutical saccharides, a plant-derived source of L-dopa, botanical regulators of insulin and IGF-1, and L-alpha glycerylphosphoryl choline (alpha GPC). By also including 7-keto DHEA, the dietary supplements of the present invention may provide further and significant anti-aging enhancements or improvements as compared to supplements and methods employing only the secretagogue. Although the present invention is not to be limited by any theoretical explanation, it is believed that a coaction exists between the glycoamino acid complex of the secretagogue and 7-keto DHEA. Such glycoamino acid complex consists of L-glutamine, L-arginine pyroglutamate, L-lysine monohydrochloride, glycine, and gamma aminobutyric acid. The combination of those amino acids with 7-keto DHEA is believed to bring the hypothalamus, pituitary, and adrenal axis into balance. This is accomplished by an interaction of 7-keto DHEA and the glycoamino acid complex resulting in the ability to down-regulate cortisol levels, which play an antagonistic role in the ability of receptor sites to be used, and helping to normalize insulin levels. With cortisol and insulin levels in the appropriate balance, the combination is believed to re-sensitize receptor sites on each of these three organs, as well as at the cellular level. When the cellular and organ receptor sites are at maximum sensitivity, they operate more efficiently, thereby allowing the rest of the ingredients of the dietary supplement to be more effective.

7-keto DHEA, whose scientific name is 3-beta-acetoxyandrost-5-en-7,17-dione, is a naturally-produced metabolite of DHEA, and scientists have postulated that it is the metabolites of DHEA that are the true active ingredients since no specific receptors in the body have been identified for DHEA itself. Researchers have since discovered that such hypothesis is correct and, more specifically, that in hormone therapy 7-keto DHEA significantly outperforms DHEA in areas such as immune modulation, memory enhancement, and thermogenesis for weight management, all without the unwanted side effects associated with DHEA. Reference may be had to the aforementioned patents for further information on 7-keto DHEA, identified generally under the designation "androstenes" in such patents. 7-keto DHEA is well known and commercially available, one such source being Humanetics Corporation, Chanhassen, Minn.

The dietary supplement compositions of this invention may be provided in liquid or powder form, with powders suitable for mixing with water or other liquids, and for ingestion as a beverage, being preferred. The amount of such powder needed for a recommended daily serving depends, of course, on the extent to which additional ingredients are included, and in that regard, the supplement of this invention is preferably formulated to include a complex of ingredients that deliver antioxidants to support the healthy functioning of major systems and to halt damage caused at the cellular level by the presence of free radicals, and natural herbs such as ginkgo, biloba and maca powder believed to play roles in reducing memory loss, promoting healthy brain function, and eliminating harmful toxins. Natural and artificial flavoring agents are also included, as well as agents that promote processing and increase solubility. The result is a blend in powder form of which a daily serving falls within the general range of about 10 g to about 30 g, the preferred serving size being approximately 16 g. In a serving of 10 g to 30 g, the secretagogue (Smybiotropin with GPC) should constitute about 600 to 1900 mg and the 7-keto DHEA component about 15 to 50 mg, so that it is believed in a preferred serving of 16 g total supplement there should be about 1000 mg secretagogue and about 25 mg 7-keto DHEA.

The antioxidant complex of a food supplement embodying this invention may include coenzyme Q10 (CoQ10), trans-resveratrol, alpha-lipoic acid, L-glutathione, and n-acetyl cysteine.

CoQ10 is a known antioxidant that is considered an important part of the metabolic process. It is involved in the energy process and can be synthesized in the body. Studies have revealed that CoQ10 holds promise in the treatment of a wide variety of degenerative diseases including diabetes, stroke, cancer and especially heart disease. In a dietary supplement embodying this invention, CoQ10 is preferably present in the range of about 4–10 mg per serving.

Alpha-lipoic acid is a recognized vitamin-like antioxidant that is sometimes referred to as the universal antioxidant because it is soluble in both fat and water. It is capable of coacting with and regenerating several other antioxidants over to their active states, including vitamin C, vitamin E, CoQ10, and L-glutathione. A synergistic effect is therefore believed to occur through the interaction of alpha-lipoic acid and such other antioxidants, with such interaction effectively boosting the power of CoQ10 and L-glutathione as well as other antioxidants found in this nutritional supplement and in fruits and vegetables that are part of a healthy diet.

L-glutathione is made up of three amino acids and is produced in all cells of the body. It functions to break down and dispose of potentially dangerous toxins and serves as an antioxidant to cleanse fatty foods of free radical hazards in the digestive track. In connection with the aging process, it has been noted that the blood levels of L-glutathione drop about 17 percent between the ages of 40 and 60. In a preferred dietary supplement embodying this invention, a daily serving contains about 30 to 95 mg of alpha-lipoic acid and about 18 to 57 mg of L-glutathione.

Resveratrol is an antioxidant, cardioprotectant and antimutagenic agent and is believed responsible for many of the health benefits attributed to red wine. A particularly potent form of resveratrol known as trans-resveratrol is derived from the root of Polygonum cuspidatum. A proprietary product, "Protykin" from Interhealth, Benicia, Calif., contains more than 400 times the resveratrol found in grape-derived sources. Protykin also contains emodin which is reported to have antimutagenic, antibacterial, and gastroprotectant properties. In a preferred embodiment of the dietary supplement of this invention, in which resveratrol, trans-resveratrol and emodin are provided by Protykin, the amount of such Protykin in a daily serving of the supplement may fall within the range of about 6 to 19 mg. Most desirably, a further antioxidant also believed to have antimutagenic properties, n-acetyl cysteine, may also be present in the range of about 125 to 375 mg.

Other ingredients included in the preferred dietary supplement of this invention because of their reported beneficial effects on sustained health and longevity are: s-adenosyl-L-methionine, omega-3 fatty acids, trimethyl glycine, a probiotic blend of *Bifidobacterium bifidum* and *Lactobacillus acidophilus,* fruco-oligosaccharides, and acetyl-L-carnitine. The first of these, s-adenosyl-L-methionine, is often referred to as SAMe and is a nontoxic natural metabolite of methionine and amino acid. Clinical trials involving more than 22,000 osteoarthritis patients support the efficacy and tolerability of SAMe in treating those suffering from the disease. Other clinical tests have produced similar results. In addition, SAMe has been shown to be an effective and quick-acting antidepressant for patients suffering from major depression.

Omega fatty acids are found in many kinds of fish oils and various other oils, including flaxseed oil and linseed oil, and numerous studies have shown clinical benefits following ingestion of omega n-3 fatty acids in patients suffering from rheumatoid arthritis. Omega-3 fatty acids, when administered orally in small doses, has also been shown to have significant positive effects on platelet activity, and such omega fatty acids are also believed to be useful in the treatment and prevention of cancer. Such omega-3 fatty acids are available in different forms, including powders consisting of fish oil distributed in a food starch-coated matrix of either gelatin or caseinate, with such powders being commercially available from BASF Corporation, St. Louis, Mo., under the proprietary designation "Dry n-3" powders.

Trimethylglycine (TMG)is being recognized for its cardiovascular benefits in promoting healthy homocysteine levels. Homocysteine is a toxic end product of the metabolism of methionine, an essential amino acid found in many foods. When the right cofactors are present, the body recycles homocysteine back to methionine, or to another essential amino acid, cysteine. However, if dietary insufficiencies exist, such insufficiencies can lead to abnormally high levels of homocysteine, which in turn may irrate the linings of vessels and arteries. Researchers now believe that such irritation can lead to cardiovascular deterioration. Studies have shown that TMG in combination with other dietary supplements helps to promote healthy homcysteine levels.

The probiotic blend of *Bifidobacterium bifidum* and *Lactobacillus acidophilus,* and the fructo-oligosaccharides, are included in the dietary supplement of this invention to promote intestinal health by increasing and maintaining intestinal flora. The components of the probiotic blend are commercially available from various sources, one such source being Nutraceutix, Inc., Redmond, Wash. The frutco-oligosaccharides are also available in different products, one such product being "BeFlora Plus" available from Roxlor International Manasquan, N.J., and consisting of frutco-oligosaccharide fiber from beets and soy protein extracts which are enriched with potassium salts and glycolate.

Acetyl-L-carnitine has been the subject of numerous scientific studies showing that such compound may be key in maintaining normal brain and nerve function during aging. These include its actions on acetylcholine synthesis, membrane stability, nerve growth factor production, and cerebral blood flow. In a preferred embodiment of the invention, acetyl-L-carnitine is present in the range of about 60 to 190 mg per daily serving, with the optimal amount being approximately 100 mg. For other ingredients discussed above, the ranges are as follows: s-adenosyl-L-methionine, 3 to 10 mg; omega-3 fatty acid powder ("Dry n-3"), 75 to 235 mg; trimethyl glycine, 60 to 190 mg; probiotic blend, 60 to 190 mg; fructo-oligosaccharides ("BeFlora Plus"), 250 to 750 mg.

The dietary supplement may also include a herbal blend composed of herbs having properties identified with anti-aging, such as ginkgo biloba (*Salsburia adiantifolia*), spirulina (*Spirulina platensis*), maca tuber powder (*Lepidium menyii*), wild yam root powder (*Dioscorea villosa* L.), Chlorella powder, diosmin, and quercetin dihydrate. Ginkgo biloba is well known for its properties as an antioxidant and spirulina, which is the dried blue-green algae of *Spirulina platensis* (family Ooscillatoriaceae) is a nutritional substance that is known to remove toxins from the bloodstream. Maca is a Peruvian crop that displays a high nutritional value and is rich in sugars, protein, starches and minerals. In recent years it has found use as a dietary supplement in improving physical and mental health, enhancing metal clarity, and increasing energy, stamina, and endurance for athletes. Similar properties are ascribed to wild yam root powder and nettle leaf powder. Chlorella has a long list of recognized health benefits, including enhancing the immune system by stimulating the body to make more interferon, increasing the number of beneficial flora in the gastrointestinal tract, promoting better digestion, reducing serum cholesterol, and increasing energy. Diosmin is a bioflavonoid derived from hesperidin, which is found in plants or citrus rinds. In addition to enhancing capillary resistance and improving venous tone, it has anti-inflammatory and antioxidant activity. Diosmin is also understood to protect the venus wall matrix and smooth muscle integrity by inhibiting the enzymes that weaken vein walls. Quercetin dihydrate is also a flavonoid that has anti-inflammatory and antioxidant activity that is understood to detoxify and thereby assist the body's ability to inhibit cancer in all human organs. While the proportions of these ingredients may be varied considerably in a daily serving of a preferred embodiment of the nutritional supplement of this invention, each may be present in the general range of about 18 to 60 mg, with the preferred amount being about 30 to 35 mg.

Various natural or artificial flavoring components and conventional food supplement additives may be included in the total composition. Such ingredients may include maltodextrin—a free-flowing carbohydrate having low sweetness, a high rate of solution, and excellent particulate strength-fructose, citric acid, dipotassium phophate, and potassium citrate. Lecithin is a phospholipid that in this dietary supplement facilitates mixing and processing, plates the particulate ingredients of the mixture and improves solubility of the final product.

The following examples are not intended to be limiting in any way, but demonstrate certain of the preferred embodiments of the present invention.

EXAMPLE 1

An essentially dry powder constituting a dietary supplement of this invention, to be dissolved in water to provide a daily serving, comprising the following ingredients in the proportions indicated: 7-keto DHEA 25 mg, Symbiotropin 1000 mg, lecithin 200 mg, maltodextrin 7,227 mg, citric acid 640 mg, dipotassium phosphate 25 mg, potassium citrate 25 mg, probiotic blend 100 mg, fruco-oligosaccharides 400 mg, s-adenosyl-L-methionine 5 mg, acetyl-L-carnitine 100 mg, omega-3 fatty acids (Dry n-3) 125 mg, trimethylglycine 100 mg, coenzyme Q10 7.5 mg, resveratrol (Protykin) 10 mg, alpha-lipoic acid 50 mg, L-glutathione 30 mg, n-acetylcysteine 200 mg, flavoring agents 300 mg.

Using a conventional plow blender set for continuous mixing, the fructose is introduced into the mixing chamber with the blender in operation. Lecithin is then gradually added and the choppers are turned on for approximately 2 minutes, followed by the addition of the other dry ingredients in the following sequence: maltodextrin, citric acid, dipotassium phosphate, potassium citrate, 7-keto DHEA, Symbiotropin, probiotic blend, BeFlora Plus, coenzyme Q10, S-adenosyl-L-methionine, Protykin, alpha-lipoic acid, acetyl-L-carnitine, Dry n-3, glutathione, TMG, flavoring agents, n-actylcysteine, and xanthan gum. The choppers are again turned on for a period of an additional two minutes to produce a uniformly-mixed dietary supplement embodying the invention.

EXAMPLE 2

The dietary supplement of Example 1 may include a herbal blend composed of the following ingredients, each being present in the amount of 31.3 mg: ginkgo biloba leaf power, queracetin dihydrate, spirulina, maca tuber powder, chlorella powder, diosmin, nettle leaf powder, wild yam root powder.

The process is the same as described in Example 1 with such ingredients of the herbal blend being sequentially introduced into the mixing chamber after the addition of Symbiotropin and before the introduction of the probiotic blend.

The dietary supplement prepared in accordance with this example takes the form of a fine light-green powder to be consumed enterally as beverage. One scoop (about 16 g) of the essentially dry mixture is added to water while stirring vigorously until dissolved. This recommended daily serving should be consumed on a relatively empty stomach to maximize the effect and benefits of the Symbiotropin/7-keto DHEA combination, as well as that of the other ingredients of the dietary supplement.

While in the foregoing we have disclosed embodiments of the invention in considerable detail for purposes of illustration, it will be understood by those skilled in the art that many of these details may be varied without departing from the spirit and scope of the invention.

What is claimed is:

1. A dietary supplement for promoting healthy hormonal balance in adult human subjects, comprising 7-keto dehydroepiandrosterone in combination with a pituitary secretagogue comprising a glycoamino acid complex of L-glutamine, L-arginine pyroglutamate, L-lysine monohydrochloride, glycine, and gamma aminobutyric acid.

2. The dietary supplement of claim 1 in which said pituitary secretagogue also comprises anterior pituitary peptides, pharmaceutical saccharides, a plant-derived source of L-dopa, and L-alpha glycerlphospheryl choline.

3. The dietary supplement of claim 1 or 2 in which said 7-keto dehydroepiandrosterone and said pituitary secretagogue are in the form of a dry powder mixture to be dissolved in an aqueous fluid for consumption as a beverage.

4. The dietary supplement of claim 3 in which a daily serving of said dietary supplement comprises about 15 to 50 mg weight of dry powder of 7-keto dehydroepiandrosterone and about 600 to 1900 mg weight of dry powder of said pituitary secretagogue.

5. The dietary supplement of claim 3 in which said supplement also includes antioxidants and a herbal blend in powder form.

6. The dietary supplement of claim 5 in which said antioxidants comprise coenzyme Q10, alpha-lipoic acid, and L-glutathione.

7. The dietary supplement of claim 6 in which the dry weights of said antioxidants for a daily serving of said supplements are 4 to 10 mg coenzyme Q10, 30 to 95 mg alpha-lipoic acid, and 18 to 57 mg L-glutathione.

8. The dietary supplement of claim 6 in which said antioxidants also comprise n-acetyl cysteine and an antioxidant blend of resveratrol, trans-resveratrol, and emodin in powder form.

9. The dietary supplement of claim 8 in which the dry weights of said n-acetyl cysteine and said antioxidant blend for a daily serving of said supplment comprises about 125 to 375 mg of n-acetyl cysteine and about 6 to 19 mg of said antioxidant blend.

10. The dietary supplement of claim 5 in which said herbal blend includes *Salsburia adiantifolia, Spirulina plastensis, Lepidium menyii, Dioscorea villosa* L., Chlorella powder, diosmin, and quercetin dihydrate.

11. A dietary supplement for promoting healthy hormonal balance in adult human subjects, comprising 7-keto dehydroepiandrosterone in combination with a pituitary secretagogue comprising glycoamino acid complex, pharmaceutical saccharides, a plant-derived source of L-dopa, botanical regulators of insulin and IGF-1, and L-alpha glycerlphosphoryl choline, said glycoamino acid complex comprising L-glutomine, L-arginine pyroglutamate, L-lysine monohydrochloride, glycine, and gamma aminobutyric acid, said supplement also including s-adenosyl-L-methionine, omega-3 fatty acids, trimethyl glycine, a probiotic blend of *Bifidobacterium bifidum* and *Lactobacillus acidophilus,* fructo-oligosaccharides, and acetyl-L-carnitine.

12. The dietary supplement of claim 11 in which the ingredients thereof are in dry powder form to be mixed with an aqueous fluid for daily consumption as a beverage.

13. The dietary supplement of claim 12 in which a daily serving of said supplement includes said ingredients in the following dry weights: said 7-keto dehydroepiandrosterone, 15 to 50 mg; said pituitary secretagogue, 600 to 1900 mg; said s-adenosyl-L-methionine, 3 to 10 mg; said omega-3 fatty acids, 75 to 235 mg; trimethyl glycine, 60 to 190 mg; said probiotic blend, 60 to 190 mg; said fructo-oligosaccharides, 250 to 750 mg; acetyl-L-carnitine, 60 to 190 mg.

14. The dietary supplement of claim 13 in which said supplement also includes antioxidants and a herbal blend in powder form.

15. The dietary supplement of claim 14 in which said antioxidants comprise coenzyme Q10, alpha-lipoic acid and L-glutathione.

16. A dietary supplement of claim 15 in which the dry weights of said antioxidants for a daily serving of said supplement are 4 to 10 mg coenzyme Q10, 30 to 95 mg alpha-lipoic acid, and 18 to 75 mg L-glutathione.

17. A dietary supplement of claim 16 in which said antioxidants also comprise n-acetyl cysteine and an antioxidant blend of reservatrol, trans-resverstrol, and emodin in powdered form.

18. The dietary supplement of claim 17 in which the dry weights of said n-acetyl cysteine and said antioxidant blend for daily serving of said supplement comprises about 125 to 375 mg of n-acetyl cysteine and about 6 to 19 mg of said antioxidant blend.

19. The dietary supplement of claim 14 in which said herbal blend includes *Salsburia adiantifolia, Spirulina plastensis, Lepidium menyii, Dioscorea villosa* L., Chlorell powder, diosmin, and quercetin dihydrate.

20. A dietary supplement in the form of a dry powder to be mixed with an aqueous fluid as a daily serving, comprising 15 to 50 mg of 7-keto dehydroepiandrosterone, 600 to 1900 mg of a pituitary secretagogue comprising glycoamino acid complex, pharmaceutical saccharides, a plant-derived source of L-dopa, botanical regulators of insulin and IGF-1, and L-alpha glycerylphosphoryl choline, said glycoamino acid complex comprising L-glutamine, L-arginine pyroglutamate, L-lysine monochydrochloride, glycine and gamma aminobutyric acid, said supplement also including 3 to 10 mg s-adenosyl-L-methionine, 75 to 235 mg omega-3 fatty acids, 60 to 190 mg, trimethyl glycine, 60 to 190 mg probiotic blend of *Bifidobacterium bifidum,* and *Lactobacillus acidophilus,* 250 to 750 mg fructo-oligosaccharides, and 60 to 190 mg acetyl-L-carnitine, said supplement also including antioxidants and a herbal blend.

21. The dietary supplement of claim 20 in which said antioxidants comprise 4 to 10 mg coenzyme Q10, 30 to 95 mg alpha-lipoic acid, and 18 to 57 mg L-glutothione.

22. The dietary suupplement of claim 21 in which said antioxidants also comprise 125 to 375 mg of n-acetyl cysteine and about 6 to 19 mg of an antioxidant blend of resveratrol, trans-resveratrol, and emodin.

23. The dietary supplement of claim 22 in which said herbal blend includes *Salsburia adiantifolia, Spirulina plastensis, Lepidium menyii, Dioscorea villosa* L.l, Chlorella powder, diosmin, and quercetin dihydrate, each of the ingredients of said herbal blend being present in the range of about 18 to 60 mg.

24. The dietary supplement of claim 23 in which the dry powder ingredients of said supplement for an adult daily serving are about 25 mg 7-keto dehydroepiandrosterone, about 1000 mg of said pituitary secretagogue, about 5 mg s-adenosyl-L-methionine, about 125 mg of omega-3 fatty acids, about 100 mg trimethyl glycine, about 100 mg of said probiotic blend, about 400 mg fructo-oliogosaccharides, about 100 mg acetyl-L-carnitine, about 7.5 mg coenzyme Q10, about 50 mg alpha-lipoic acid, about 30 mg L-glutathione, about 200 mg n-acetyl cysteine, about 10 mg of said antioxidant blend, and about 31.3 mg each of said *Salsburia adiantifolia, Spirulina plastensis, Lepidium menyii, Dioscorea villosa* L., Chlorella powder, diosmin, and quercetin dihydrate.

\* \* \* \* \*